(12) United States Patent
Morita

(10) Patent No.: US 9,805,449 B2
(45) Date of Patent: Oct. 31, 2017

(54) RADIATION IMAGE PROCESSING APPARATUS AND METHOD

(71) Applicant: FUJIFILM Corporation, Tokyo (JP)

(72) Inventor: Junya Morita, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 127 days.

(21) Appl. No.: 14/566,077

(22) Filed: Dec. 10, 2014

(65) Prior Publication Data

US 2015/0093013 A1 Apr. 2, 2015

Related U.S. Application Data

(63) Continuation of application No. PCT/JP2013/003631, filed on Jun. 10, 2013.

(30) Foreign Application Priority Data

Jun. 11, 2012 (JP) ................................ 2012-132087
Mar. 7, 2013 (JP) ................................ 2013-045502

(51) Int. Cl.
*G06K 9/00* (2006.01)
*G06K 9/38* (2006.01)
(Continued)

(52) U.S. Cl.
CPC ............... *G06T 5/009* (2013.01); *A61B 6/50* (2013.01); *A61B 6/502* (2013.01); *A61B 6/5205* (2013.01);
(Continued)

(58) Field of Classification Search
None
See application file for complete search history.

(56) References Cited

U.S. PATENT DOCUMENTS 8,340,380 B2 12/2012 Morita
8,600,126 B2 12/2013 Morita
(Continued)

FOREIGN PATENT DOCUMENTS

JP 7-248558 A 9/1995
JP 8-66389 A 3/1996
(Continued)

OTHER PUBLICATIONS

International Search Report for PCT/JP2013/003631 dated Sep. 10, 2013.
(Continued)

*Primary Examiner* — Randolph I Chu
(74) *Attorney, Agent, or Firm* — Birch, Stewart, Kolasch & Birch, LLP

(57) ABSTRACT

A composition information obtaining unit calculates a mammary gland/fat ratio and a first information obtaining unit obtains imaged contrast information representing a contrast of the radiation image. A second information obtaining unit sets target application condition of X-ray, and obtains target contrast information representing an intended contrast for the radiation image based on the intended application condition. A contrast correction amount determination unit determines a contrast correction amount based on the imaged contrast information and the target contrast information. An image processing unit performs image processing, including gradation processing based on the determined contrast correction amount, on the radiation image, and obtains a processed radiation image.

14 Claims, 13 Drawing Sheets

(51) Int. Cl.
  *G06K 9/40* (2006.01)
  *G06T 5/00* (2006.01)
  *A61B 6/00* (2006.01)
  A61B 6/04 (2006.01)
  *H05G 1/32* (2006.01)

(52) U.S. Cl.
  CPC .......... *A61B 6/5211* (2013.01); *A61B 6/5258* (2013.01); *A61B 6/583* (2013.01); *A61B 6/0414* (2013.01); *A61B 6/4035* (2013.01); *A61B 6/4291* (2013.01); *A61B 6/544* (2013.01); *A61B 6/545* (2013.01); *A61B 6/588* (2013.01); *A61B 6/589* (2013.01); *G06T 2207/10116* (2013.01); *G06T 2207/20208* (2013.01); *G06T 2207/30068* (2013.01); *H01J 2235/00* (2013.01); *H05G 1/32* (2013.01)

(56) References Cited

U.S. PATENT DOCUMENTS

| | | | |
|---|---|---|---|
| 2003/0058464 A1* | 3/2003 | Loveridge | H04N 1/6027 358/1.9 |
| 2004/0042680 A1* | 3/2004 | Saund | H04N 1/6027 382/274 |
| 2004/0081273 A1* | 4/2004 | Ning | A61B 6/032 378/37 |
| 2005/0069184 A1* | 3/2005 | Kasai | G06T 7/0012 382/128 |
| 2009/0087045 A1* | 4/2009 | Partain | G06T 7/0012 382/128 |
| 2009/0252396 A1* | 10/2009 | Morita | G06T 7/0081 382/132 |
| 2010/0246921 A1 | 9/2010 | Iwami et al. | |
| 2010/0246924 A1* | 9/2010 | Morita | A61B 5/4872 382/132 |
| 2010/0266508 A1* | 10/2010 | Kattumuri | A61K 49/0428 424/9.42 |
| 2010/0316267 A1* | 12/2010 | Buelow | G06T 7/0083 382/128 |
| 2011/0206257 A1* | 8/2011 | Qanadli | A61B 5/02014 382/130 |
| 2011/0229004 A1* | 9/2011 | Buelow | G06T 7/0012 382/131 |
| 2011/0280494 A1* | 11/2011 | Da Rocha Leitao | G06T 5/20 382/274 |
| 2012/0257808 A1* | 10/2012 | Spitzer | G06T 5/008 382/131 |
| 2013/0051644 A1* | 2/2013 | Nett | G06T 11/008 382/131 |
| 2013/0051676 A1* | 2/2013 | Wehnes | G06T 7/0012 382/190 |
| 2013/0142304 A1* | 6/2013 | Shiraishi | G01N 23/02 378/51 |
| 2013/0281819 A1* | 10/2013 | Schmid | A61B 5/0095 600/407 |
| 2013/0296683 A1* | 11/2013 | Herzog | A61B 5/0095 600/407 |
| 2013/0296684 A1* | 11/2013 | Miller | A61B 5/0095 600/407 |
| 2013/0296701 A1* | 11/2013 | Zalev | A61B 5/0095 600/440 |
| 2013/0304405 A1* | 11/2013 | Schmid | G01H 1/003 702/56 |
| 2014/0093150 A1* | 4/2014 | Zalev | G06T 7/0012 382/131 |
| 2015/0075287 A1* | 3/2015 | Herzog | A61B 8/4281 73/655 |
| 2015/0093013 A1* | 4/2015 | Morita | A61B 6/502 382/132 |

FOREIGN PATENT DOCUMENTS

| | | |
|---|---|---|
| JP | 2001-86409 A | 3/2001 |
| JP | 2009-247521 A | 10/2009 |
| JP | 2010-131179 A | 6/2010 |
| JP | 2010-233997 A | 10/2010 |
| JP | 2010-253245 A | 11/2010 |
| JP | 2010-277231 A | 12/2010 |
| JP | 2011-239804 A | 12/2011 |
| JP | 2012-100734 A | 5/2012 |

OTHER PUBLICATIONS

Written Opinion of the International Searching Authority for PCT/JP2013/003631 dated Sep. 10, 2013.

* cited by examiner

FIG.5

| BREAST THICKNESS [mm] | TARGET APPLICATION CONDITION | | ~T1 |
|---|---|---|---|
| | T/F | TUBE VOLTAGE [kV] | |
| 0-20 | Mo/Mo | 26 | |
| -30 | Mo/Mo | 27 | |
| -35 | Mo/Mo | 28 | |
| -45 | Mo/Rh | 28 | |
| -50 | Mo/Rh | 28 | |
| -55 | Mo/Rh | 29 | |
| -60 | Mo/Rh | 30 | |
| -65 | W/Rh | 29 | |
| -90 | W/Rh | 30 | |
| 90- | W/Rh | 32 | |

FIG.6

THICKNESS [mm]

| W/Rh | 20 | 40 | 60 | 80 |
|---|---|---|---|---|
| 23 | 1.03 | 0.93 | 0.87 | 0.83 |
| 25 | 0.93 | 0.84 | 0.78 | 0.75 |
| 27 | 0.90 | 0.81 | 0.76 | 0.72 |
| 29 | 0.87 | 0.79 | 0.73 | 0.69 |
| 31 | 0.85 | 0.76 | 0.70 | 0.65 |
| 33 | 0.82 | 0.72 | 0.65 | 0.60 |
| 35 | 0.78 | 0.68 | 0.60 | 0.54 |

TUBE VOLTAGE [kV]

| Mo/Mo | 20 | 40 | 60 | 80 | T2 |
|---|---|---|---|---|---|
| 23 | 1.26 | 1.13 | 1.06 | 1.01 | |
| 25 | 1.20 | 1.07 | 0.98 | 0.90 | |
| 27 | 1.15 | 1.03 | 0.93 | 0.83 | |
| 29 | 1.11 | 0.97 | 0.85 | 0.73 | |
| 31 | 1.07 | 0.91 | 0.77 | 0.65 | |
| 33 | 1.04 | 0.86 | 0.71 | 0.58 | |
| 35 | 1.00 | 0.81 | 0.65 | 0.52 | |

THICKNESS [mm] →

TUBE VOLTAGE [kV] ↓

RADIATION IMAGE PROCESSING APPARATUS AND METHOD

CROSS-REFERENCE TO RELATED APPLICATIONS

This application is a Continuation of PCT International Application No. PCT/JP2013/003631 filed on Jun. 10, 2013, which claims priority under 35 U.S.C. §119 (a) to Japanese Patent Application No. 2012-132087 filed on Jun. 11, 2012 and Japanese Patent Application No. 2013-045502 filed on Mar. 7, 2013. Each of the above applications is hereby expressly incorporated by reference, in its entirety into the present application.

BACKGROUND OF THE INVENTION

Technical Field

The present invention relates to a radiation image processing apparatus and method that performs image processing to correct contrast or frequency characteristics of a radiation image such as, for example, a breast image.

Background Art

Image diagnosis through the use of a radiation image capturing system (called mammography) for imaging a breast has been drawing wide attention to facilitate early detection of breast cancers. A radiation image of a breast (breast image) captured by the mammography is subjected to image processing in a dedicated operation terminal or the like, and used by a doctor for diagnosis. The doctor checks for a lesion such as, for example, a tumor mass or a calcification by displaying the breast image on a display and interpreting the image.

The image processing described above is performed for ease of interpretation of the breast image. More specifically, image processing conditions for performing image processing are determined based on the breast image such that image characteristics, including density, gradation, dynamic range, frequency characteristics, and noise of a target interpretation area, become appropriate to obtain a breast image having a desired image quality, and image processing is performed according to the determined image processing conditions.

In the meantime, in capturing a radiation image, exposure dose of the subject by X-ray is preferably reduced as much as possible. Further, in order to obtain a radiation image that allows an appropriate interpretation diagnosis, X-ray having an energy spectrum corresponding to the X-ray absorption property of the imaging region needs to be applied to the subject.

For example, in the aforementioned mammography, a diseased tissue having a very small difference in X-ray absorption amount with respect to a normal tissue is extracted in high contrast, so that low energy X-rays are typically used. Further, in applying an X-ray to a subject, the use of characteristic X-ray is efficient and a target that generates an X-ray when hit by an electron beam is selected according to the X-ray absorption property of the imaging region for that purpose. In the meantime, the increase in high energy X-ray component may reduce the contrast of a radiation image while the increase in low energy component may increase the exposure dose of the subject. Thus, a filter that can selectively absorb a high energy X-ray component or a low energy X-ray component is selected according to the X-ray absorption property of the imaging region.

Commonly used target types include Mo (molybdenum), Rh (rhodium), and W (tungsten), while commonly used filter types include Mo (molybdenum) and Rh (rhodium). The use of Mo in both the target and the filter (Mo/Mo) may result in a relatively large amount of low energy X-ray component and a high contrast image quality, but the exposure dose of the subject is increased. On the other hand, the use of W in the target and Rh in the filter (W/Rh) may result in a relatively large amount of high energy X-ray component and a low contrast image quality, but the exposure dose of the subject is reduced. The radiographer sets radiation application conditions such that a desired image quality is obtained according to the subject while reducing the exposure dose as much as possible.

As described above, image processing is performed on a radiation image obtained by an imaging system. Performance of the same image processing regardless of the types of the target and the filter used, however, the image qualities may differ, which may affect the diagnosis based on the obtained radiation image. For example, a radiation image obtained by the combination of W/Rh is reduced in contrast due to a reduced density range of the image with respect to a radiation image obtained by the combination of Mo/Mo as described above. Such a trouble is a large problem when changing the target or the filter while obtaining radiation images of left and right breasts of the same subject or performing imaging by changing the imaging directions.

As such, a method is proposed that obtains an appropriate radiation image by selecting image processing conditions, including gradation processing conditions and frequency processing conditions according to X-ray application conditions, such as the type of target, the type of filter, and the tube voltage, without depending on the radiation quality (Japanese Unexamined Patent Publication No. 2010-131179).

In the meantime, parameters for gradation processing and frequency processing differ depending on the thickness of the subject. For example, the transmission amount of X-ray differs between a thick portion and a thin portion of a subject, resulting in different contrasts. For this reason, a method that measures the thickness of a subject and sets a parameter for emphasizing the contrast by performing gradation processing according to the X-ray exposure amount and the thickness (Japanese Unexamined Patent Publication No. 2012-100734), and a method that sets a parameter for frequency processing according to X-ray application conditions and a body thickness (Japanese Unexamined Patent Publication No. 2011-239804) are proposed.

DISCLOSURE OF THE INVENTION

In the meantime, adoption of an arrangement in which a plurality of materials, as the target and the filter, is switchable may pose a problem that the cost of the imaging system is increased. On the other hand, if the target and the filter cannot be selectable, the radiographer may not perform imaging with desired application conditions and a radiation image having a desired image quality may not be obtained.

Further, when the imaging system is replaced, the application conditions may differ depending on the imaging system and image qualities of radiation images obtained before and after the replacement may differ. Still further, there may be a case in which desired application conditions cannot be set due to imaging constraints. For example, in the case of chest imaging, the contrast of a bone portion overlapping with a soft portion is preferably reduced by setting the tube voltage to a relatively high value of about 100 kV to 120 kV. Portable imaging performed, for example, in a patient room, however, the tube voltage may be set only to about 80 kV due to imaging constraints. In such a case also, a radiation image having a desired image quality may not be obtained.

The radiation image quality differs depending on not only the X-ray application conditions but also the thickness and the composition of a subject. For example, the difference in radiation image quality due to application conditions tends to increase as the body thickness decreases, and to reduce as the thickness increases. The method described in Japanese Unexamined Patent Publication No. 2010-131179 is on the assumption that a radiation image obtained by the combination of W/Rh is reduced in contrast with respect to a radiation image obtained by the combination of Mo/Mo, but the combination of W/Rh may sometimes provide a higher contrast depending on the thickness of the subject. Further, the degree of variation in the radiation image quality differs depending also on the composition of the subject. For example, if the subject is a breast, the difference in contrast between a radiation image obtained by the combination of Mo/Mo and a radiation image obtained by the combination of W/Rh tends to decrease as the amount of mammary gland increases. Therefore, the consideration of only the application conditions, as in Japanese Unexamined Patent Publication No. 2010-131179, may result in that a radiation image having a desired contrast is not obtained.

In the meantime, Japanese Unexamined Patent Publication Nos. 2012-100734 and 2011-239804 describe a method that sets parameters for image processing, considering also the thickness of a subject, but the parameters are set without considering the image quality of a radiation image obtained by imaging, so that the parameters may possibly be inappropriate for the obtained radiation image. Further, the method described in Japanese Unexamined Patent Publication Nos. 2012-100734 and 2011-239804 is not a method that obtain an image with desired application conditions and cannot solve the problem when a radiographer cannot perform imaging with desired application conditions.

The present invention has been developed in view of the circumstances described above, and it is an object of the present invention to allow a radiation image having a contrast according to a desired application condition to be obtained by considering an application condition of radiation applied to a subject.

It is a further object of the present invention to allow a radiation image having a frequency characteristic according to a desired application condition to be obtained by considering an application condition of radiation to be applied to a subject.

A radiation image processing apparatus according to the present invention includes:
  a radiation image obtaining means that obtains a radiation image of a subject;
  a first information obtaining means that obtains imaged contrast information representing a contrast of the radiation image;
  a second information obtaining means that sets an intended application condition of the radiation, and obtains target contrast information representing an intended contrast for the radiation image based on the intended application condition; and
  a contrast correction amount determination means that determines a contrast correction amount for the radiation image based on the imaged contrast information and the target contrast information.

In the radiation image processing apparatus according to the present invention, the first information obtaining means may be a means that obtains the imaged contrast information based on a thickness of the subject and an application condition of the radiation at the time of obtaining the radiation image.

Further, in the radiation image processing apparatus according to the present invention, the second information obtaining means may be a means that sets the intended application condition based on a thickness of the subject, and obtains the target contrast information based on the thickness of the subject and the intended application condition.

Still further, the radiation image processing apparatus according to the present invention may further includes a storage means that stores intended application condition information corresponding to a plurality of the thicknesses of the subject and contrast information corresponding to the plurality of thicknesses of the subject and a plurality of the application conditions, wherein:
  the first information obtaining means may be a means that obtains the imaged contrast information with reference to the contrast information stored in the storage means; and
  the second information obtaining means may be a means that sets the intended application condition with reference to the application condition information, and obtains the target contrast information with reference to the contrast information stored in the storage means.

Further, the radiation image processing apparatus according to the present invention may further includes a composition information obtaining means that obtains composition information of the subject, wherein:
  the first information obtaining means may be a means that obtains the imaged contrast information based also on the composition information; and
  the second information obtaining means may be a means that obtains the target contrast information based also on the composition information.

The composition information may be ratio information of a plurality of compositions contained in the subject. More specifically, in the radiation image, it may be a ratio of a plurality of compositions obtained on a pixel basis or on a sub-area basis when the radiation image is divided into a plurality of sub-areas. Further, if the entire image is regarded as one composition, a ratio of a certain composition area to the entire image may be the composition information.

The radiation image processing apparatus according to the present invention may further include a storage means that stores intended application condition information corresponding to a plurality of the thicknesses of the subject, and contrast information corresponding to the plurality of thicknesses of the subject, a plurality of the application conditions, and a plurality of the compositions, wherein:
  the first information obtaining means may be a means that obtains the imaged contrast information with reference to the contrast information stored in the storage means; and
  the second information obtaining means may be a means that sets the intended application condition with reference to the application condition information, and obtains the target contrast information with reference to the contrast information stored in the storage means.

Further, in the radiation image processing apparatus according to the present invention, the subject may be a breast, and the composition may be a mammary gland/fat ratio.

Still further, the radiation image processing apparatus according to the present invention may further includes:

a third information obtaining means that obtains imaged frequency characteristic information representing a frequency characteristic of the radiation image;

a fourth information obtaining means that obtains target frequency characteristic information representing an intended frequency characteristic for the radiation image based on the intended application condition; and a frequency characteristic correction amount determination means that determines a frequency characteristic correction amount for the radiation image based on the imaged frequency characteristic information and the target frequency characteristic information.

In this case, the third information obtaining means may be a means that obtains the imaged frequency characteristic information based on the thickness of the subject and the application condition, and the fourth information obtaining means may be a means that sets the intended application condition based on the thickness of the subject, and obtains the target frequency characteristic information based on the thickness of the subject and the intended application condition.

Further, in the radiation image processing apparatus according to the present invention, the subject may be a breast, and if a plurality of different radiation images is obtained for the breast, the second information obtaining means may be a means that obtains target contrast information common to the plurality of radiation images.

In this case, the radiation image processing apparatus according to the present invention may further include a switching means that switches whether or not to obtain the target contrast information common to the plurality of radiation images.

A radiation image processing method according to the present invention includes the steps of:

obtaining a radiation image of a subject;

obtaining imaged contrast information representing a contrast of the radiation image;

setting an intended application condition of the radiation, and obtaining target contrast information representing an intended contrast for the radiation image based on the intended application condition; and determining a contrast correction amount for the radiation image based on the imaged contrast information and the target contrast information.

Another radiation image processing apparatus according to the present invention includes:

a radiation image obtaining means that obtains a radiation image of a subject;

a first information obtaining means that obtains imaged frequency characteristic information representing a frequency characteristic of the radiation image;

a second information obtaining means that sets an intended application condition of the radiation, and obtains target frequency characteristic information representing an intended frequency characteristic for the radiation image based on the intended application condition; and a frequency characteristic correction amount determination means that determines a frequency characteristic correction amount for the radiation image based on the imaged frequency characteristic information and the target frequency characteristic information.

In the another radiation image processing apparatus according to the present invention, the first information obtaining means may be a means that obtains the imaged frequency characteristic information based on a thickness of the subject and an application condition of the radiation at the time of obtaining the radiation image.

Further, in the another radiation image processing apparatus according to the present invention, the second information obtaining means may be a means that sets the intended application condition of the radiation based on a thickness of the subject, and obtains the target contrast information based on the thickness of the subject and the intended application condition.

Still further, the another radiation image processing apparatus according to the present invention may further include a composition information obtaining means that obtains composition information of the subject, wherein:

the first information obtaining means may be a means that obtains the imaged frequency characteristic information based also on the composition information; and the second information obtaining means may be a means that obtains the target frequency characteristic information based also on the composition information.

Further, the another radiation image processing apparatus according to the present invention may further include a storage means that stores intended application condition information corresponding to a plurality of the thicknesses of the subject and frequency characteristic information corresponding to the plurality of thicknesses of the subject and a plurality of the application conditions, wherein:

the first information obtaining means may be a means that obtains the imaged frequency characteristic information with reference to the contrast information stored in the storage means; and the second information obtaining means may be a means that sets the intended application condition with reference to the application condition information, and obtains the target frequency characteristic information with reference to the contrast information stored in the storage means.

Still further, the another radiation image processing apparatus according to the present invention may further include a storage means that stores intended application condition information corresponding to a plurality of the thicknesses of the subject, and frequency characteristic information corresponding to the plurality of thicknesses of the subject, a plurality of the application conditions, and a plurality of the compositions, wherein:

the first information obtaining means may be a means that obtains the imaged frequency characteristic information with reference to the frequency characteristic information stored in the storage means; and the second information obtaining means may be a means that sets the intended application condition with reference to the application condition information, and obtains the target frequency characteristic information with reference to the frequency characteristic information stored in the storage means.

Further, in the another radiation image processing apparatus according to the present invention, the subject may be a breast.

Still further, in the another radiation image processing apparatus according to the present invention, the subject may be a breast and the composition may be a mammary gland/fat ratio.

Another radiation image processing method according to the present invention includes the steps of obtaining a radiation image of a subject;

obtaining imaged frequency characteristic information representing a frequency characteristic of the radiation image;

setting an intended application condition of the radiation;

obtaining target frequency characteristic information representing an intended frequency characteristic for the radiation image based on the intended application condition; and determining a frequency characteristic correction amount for the radiation image based on the imaged frequency characteristic information and the target frequency characteristic information.

According to the present invention, imaged contrast information representing a contrast of a radiation image is obtained, an intended application condition of radiation is set, and target contrast information representing an intended contrast of the radiation image is obtained base on the intended application condition. Then, a contrast correction amount for the radiation image is determined based on the imaged contrast information and the target contrast information. Therefore, by correcting the contrast of the radiation image based on the determined correction amount, a radiation image having a contrast identical to that obtained when imaging is performed under a desired application condition may be obtained.

Further, a radiation image having a contrast identical to that obtained when imaging is performed under a desired application condition may be obtained even if the application condition may not be set by the imaging system.

Further, by obtaining the imaged contrast information based on the thickness of the subject and the application condition, and/or setting an intended application condition based on the thickness of the subject, and setting target contrast information based on the thickness of the subject and the intended application condition, a radiation image having a contrast identical to that obtained when imaging is performed under a desired application condition may be obtained based on the application condition of the radiation applied to the subject and the thickness of the subject.

Still further, by obtaining the imaged contrast information and the target contrast information based also on a composition of the subject, a radiation image having a contrast identical to that obtained when imaging is performed under a desired application condition may be obtained based not only on the application condition of the radiation applied to the subject but also on the thickness and the composition of the subject.

Further, if imaged frequency characteristic information representing a frequency characteristic of a radiation image is obtained, an intended application condition of radiation is set, target frequency characteristic information representing an intended frequency characteristic of the radiation image is obtained base on the intended application condition, then, a frequency characteristic correction amount for the radiation image is determined based on the imaged frequency characteristic information and the target frequency characteristic information, and the frequency characteristic of the radiation image is corrected based on the determined correction amount, a radiation image having a frequency characteristic identical to that obtained when imaging is performed under a desired application condition may be obtained.

BRIEF DESCRIPTION OF DRAWINGS

FIG. 5 shows a target application condition information table.

FIG. 6 shows a contrast table.

BEST MODE FOR CARRYING OUT THE INVENTION

Figure 1:
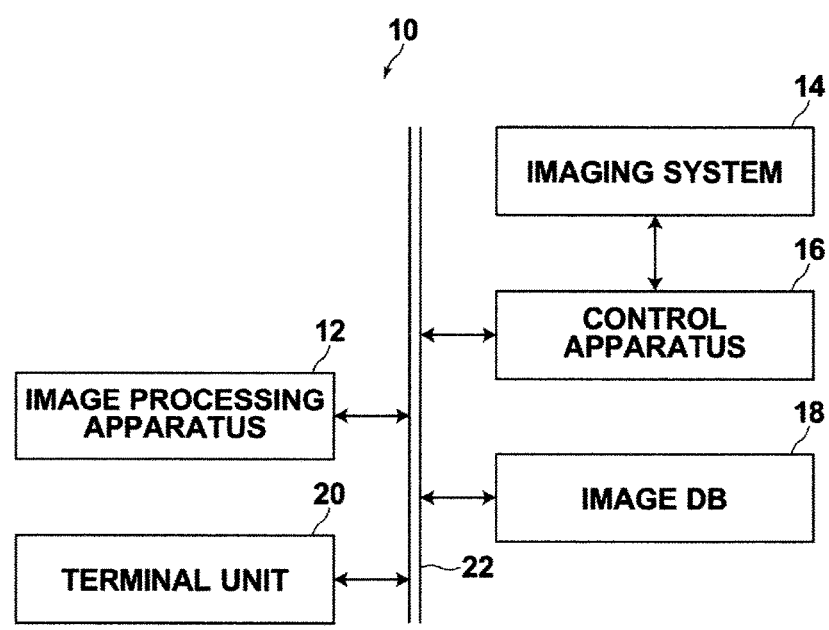
FIG. 1 is a schematic block diagram of a medical image support system that includes a radiation image processing apparatus according to a first embodiment, illustrating the configuration thereof.

Hereinafter, embodiments of the present invention will be described with reference to the accompanying drawings. FIG. 1 is a schematic block diagram of a medical image support system which includes a radiation image processing apparatus according to a first embodiment, illustrating the configuration thereof. As illustrated in FIG. 1, the system 10 includes a radiation image processing apparatus according to a first embodiment of the present invention (hereinafter, simply referred to as image processing apparatus) 12, a mammography imaging system 14 installed in a medical facility or the like, a control apparatus 16 that controls the mammography imaging system 14, an image database (image DB) 18 that stores breast images obtained by the mammography imaging system 14, and a terminal unit 20, with a high definition monitor (not shown), for a doctor that performs image interpretation. These are interconnected via a network 22.

Figure 2:
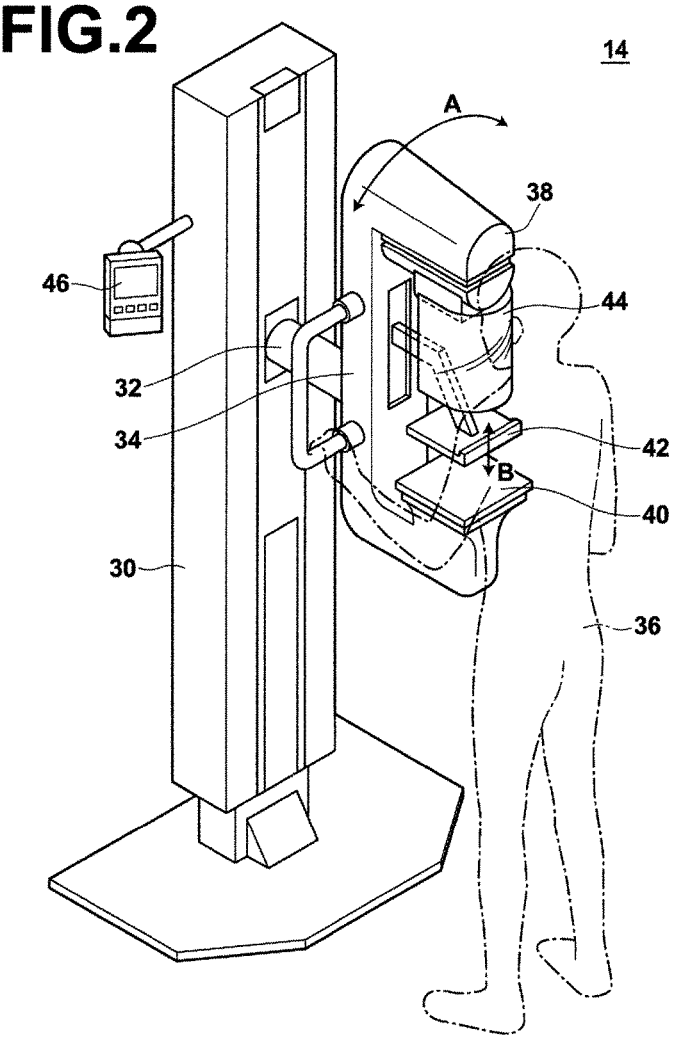
FIG. 2 is a schematic view of a mammography imaging system, illustrating the structure thereof.

FIG. 2 is a schematic view of the mammography imaging system 14, illustrating the structure thereof. As illustrated in FIG. 2, the mammography imaging system 14 includes a vertically arranged base 30, an arm member 34 fixed to a pivot shaft 32 substantially disposed in a central portion of the base 30, an X-ray source housing 38 accommodating an X-ray source that emits radiation (X-ray) to expose a breast of a subject 36 and being fixed to one end of the arm member 34, an imaging platform 40 accommodating a solid state detector that obtains a radiation image of the breast by detecting an X-ray transmitted through the breast and being fixed to the other end of the arm member 34, and a compression paddle 42 that compresses the breast against the imaging platform 40.

The arm member 34 to which the X-ray source housing 38, the imaging platform 40, and the compression paddle 42 are coupled pivots on the pivot shaft 32 in an arrow A direction in FIG. 2 to adjustably form the imaging direction with respect to the breast of the subject 36. The compression paddle 42 which is coupled to the arm member 38 is disposed between the X-ray source housing 38 and the imaging platform 40 and movably structured in an arrow B direction in FIG. 2.

A face guard sheet 44 made of a material that blocks X-rays is disposed at the X-ray source housing 38 for protecting near the face of the subject 36 from X-ray exposure. Further, an indicator 46 is disposed on the base 30 to display imaging information, including imaging region of the subject 36, imaging direction, and other information such as, for example, ID information of the subject 36, in addition to, if required, information of compression remaining time to the time when the compressed state of the breast by the compression paddle 42 will be released.

Figure 3:
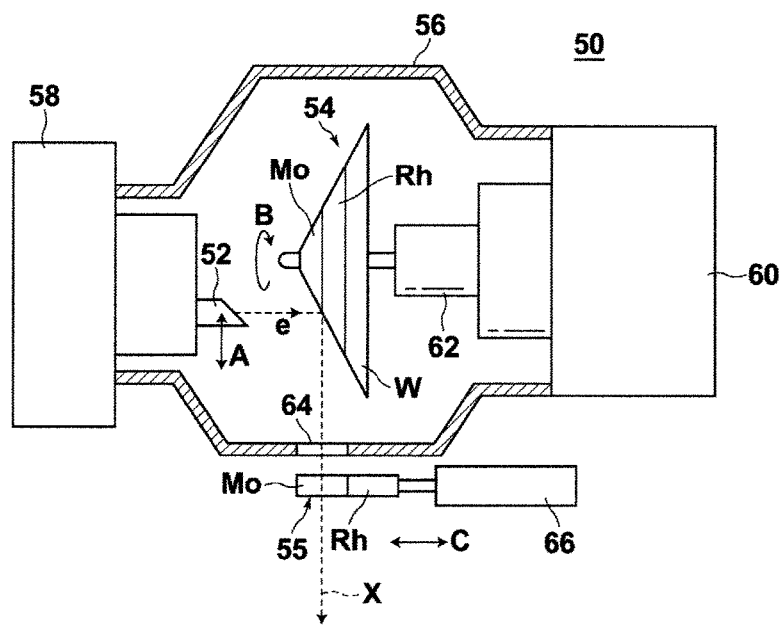
FIG. 3 is a schematic view of an X-ray source, illustrating the structure thereof.

FIG. 3 is a schematic view of an X-ray source housed in the X-ray source housing 38, illustrating the structure thereof. The X-ray source 50 includes a filament 52 that emits an electron beam e, a target 54 that generates an X-ray x when hit by an electron beam, and a filter 55 that controls the energy spectrum of the X-ray x. A predetermined tube voltage is applied between the cathode filament 52 and the anode target 54. The filament 52 and the target 54 are housed in an insulating oil-filled vacuum envelope 56. The filament 52 is held by a filament holder 58 disposed on one end of the vacuum envelope 56 and movably formed in an arrow A direction in FIG. 3. The target 54 is held by a target holder 60 disposed on the other end of the vacuum envelope 56 via a motor 62 and rotatably formed in the arrow B direction in FIG. 3.

A plurality of different anode materials, for example, Mo, Rh, and W, is disposed at different positions in the diameter direction, and the incident position of the electron beam e on the target 54 may be changed by moving the filament 52 in an arrow A direction in FIG. 3. This allows the energy spectrum of the X-ray x generated from the target 54 to be selected according to the anode material.

The X-ray x generated from the target 54 is outputted via a Be emission window 64 and applied to the imaging platform 40 through the filter 55. The filter 55 includes a plurality of different materials, for example, Mo, Rh, and W, disposed in an arrow C direction in FIG. 3 and is movably formed in an arrow C direction by a filter moving unit 66 to select a material through which the X-ray x passes. As for the materials forming the filter 55, Nb, Ag, or a composite material composed of these single materials may be used, other than those described above.

Figure 4:
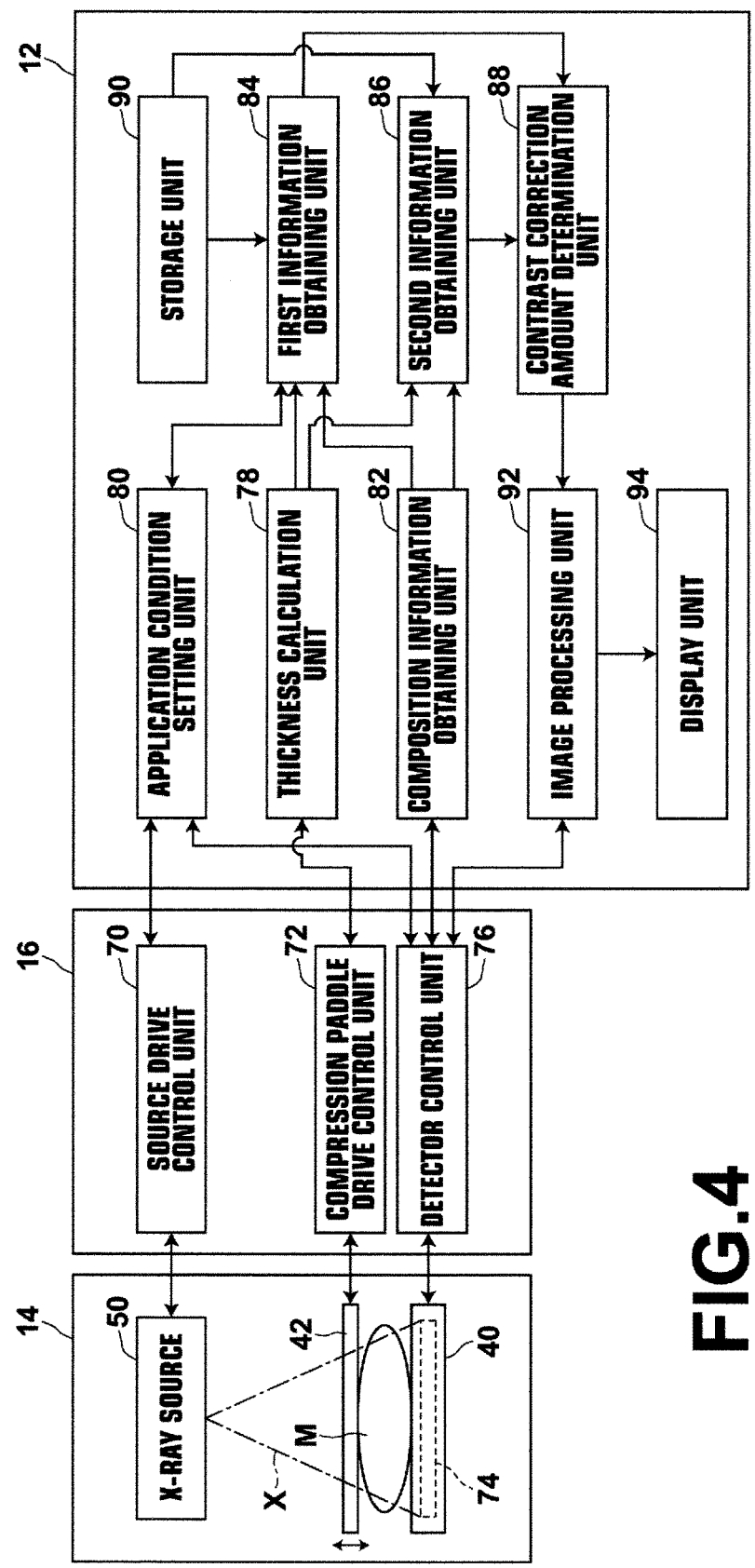
FIG. 4 is a block diagram of control circuits of the image processing apparatus, a mammography imaging system, and a control apparatus according to the first embodiment.

FIG. 4 is a block diagram of control circuits of the image processing apparatus, a mammography imaging system, and a control apparatus according to the first embodiment. The control apparatus 16 that controls the mammography imaging system 14 includes a source drive control unit 70 that drive controls the X-ray source 50 according to the given application conditions, a compression paddle drive control unit 72 that drive controls the compression paddle 42 and compresses a breast M of the subject 36 against the imaging platform 40, and a detector control unit 76 that controls a solid-state detector 74 accommodated in the imaging platform 40 to obtain a radiation image.

The image processing apparatus 12 includes a thickness calculation unit 78 that calculates a thickness of the breast M based on the position information of the compression paddle 42 supplied from the compression paddle drive control unit 72, an application condition setting unit 80 that sets application conditions to be set to the X-ray source 50, a composition information obtaining unit 82 that obtains a mammary gland/fat ratio of the breast M as composition information of the breast M by the use of a radiation image supplied from the detector control unit 76, a first information obtained unit 84 that obtains imaged contrast information representing a contrast of the radiation image based on the composition information, the thickness information of the breast M, and the application conditions, and a second information obtaining unit 86 that sets intended application conditions (target application conditions) for the X-ray based on the thickness of the breast M and obtains target contrast information representing an intended contrast for the radiation image based on the composition information, the thickness of the breast M, and the target application conditions. The image processing apparatus 12 further includes a contrast amount correction determination unit 88 that determines a contrast correction amount for the radiation image based on the imaged contrast information and the target contrast information, a storage unit 90 that stores target application condition information corresponding to a plurality of thicknesses of the breast M, and contrast information corresponding to a plurality of thicknesses of the breast M, a plurality of application conditions, and a plurality of mammary gland/fat ratios with respect to each combination of target and filter, an image processing unit 92 that performs predetermined image processing, including gradation processing based on a corrected contrast, on the radiation image supplied from the detector control unit 76, and a display unit 94 that displays an image processed radiation image.

The application conditions described above refer to conditions for obtaining an appropriate radiation image by controlling the energy spectrum (radiation quality) of the X-ray x applied to the breast M. Such conditions may include, for example, a type of the target 54 of the X-ray source 50, a type of filter 55, a tube voltage applied between the filament 52 and the target 54, and a mAs value (tube current×radiation application time). The image processing conditions may include, for example, a standardization processing condition, an edge enhancement processing condition, a frequency processing condition, a noise filtering processing condition, a dynamic range adjustment processing condition, and a gradation processing condition for the radiation image.

The image processing unit 92 may first perform gradation processing on the obtained radiation image based on the corrected contrast, then perform image processing (including gradation processing) based on predetermined image processing conditions. Further, no gradation processing may be performed in the image processing after the gradation processing based on the corrected contrast is performed. In the present embodiment, a description will be made of a case in which image processing, including gradation processing, is performed in the image processing after the gradation processing based on the corrected contrast is performed.

Here, the information of the target application conditions corresponding to a plurality of thicknesses of the breast M and the contrast information stored in the storage unit 90 will be described. FIG. 5 shows a target application condition information table. As shown in FIG. 5, Table T1 of the target application condition information defines target application conditions corresponding a plurality of breast thicknesses. Here, T/F that indicates types of target and filter, and tube voltage are set as the target application conditions. For example, if the breast thickness is 43 mm, the T/F is set to Mo/Rh (target is Mo and filter is Rh) and the tube voltage is set to 28 kV as the target application conditions with reference to Table T1.

FIG. 6 shows a table that defines contrast information (Contrast Table). As shown in FIG. 6, Contrast Table T2 is a three-dimensional table that defines contrasts corresponding to a plurality of breast thicknesses, a plurality of tube voltages, and a plurality of mammary gland/fat ratios with respect to each combination of target and filter. Note that Contrast Table T2 shown in FIG. 6 defines contrasts corresponding to a plurality of breast thicknesses and a plurality of tube voltages when the combination of target and filter is W/Rh and the mammary gland/fat ratio is 50%. Although FIG. 6 illustrates Contrast Table T2 as a two-dimensional table, but it is actually a three-dimensional table in which the two-dimensional table shown in FIG. 6 is defined corresponding to a plurality of mammary gland/fat ratios. Contrast Table T2 as shown, for example, in FIG. 6 discretely defines the breast thickness, the tube current, and the mammary gland/fat ratio at intervals of 20 mm, 2 kV, and for example 10% for the breast thickness, the tube current, and the mammary gland/fat ratio respectively, but a contrast value for a breast thickness, a tube voltage, or a mammary gland/fat ratio not defined in Contrast Table T2 may be calculated through interpolation using contrast values of adjacent breast thickness values, tube voltage values, or mammary gland/fat ratio values.

Figure 7:
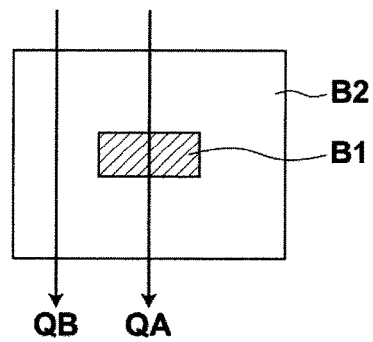
FIG. 7 is a drawing for explaining contrast calculation by simulation.

Note that the contrasts defined in Contrast Table T2 are calculated by simulation. In the present embodiment, the difference between a signal value of a radiation image on the assumption that the mammary glands occupy by 50% (i.e., the mammary gland/fat ratio is 50%) and a signal value of a radiation image on the assumption that mammary glands with a thickness of 5 mm occupy by 100% (i.e., mammary gland/fat ratio is 100%) inside of a background with the mammary gland/fat ratio of 50% is defined as the contrast. FIG. 7 is a drawing for explaining contrast calculation by simulation. As shown in FIG. 7, a subject having a predetermined thickness defined in Contrast Table T2 is assumed and a tissue B1 of 100% mammary gland (mammary gland tissue) with a thickness of 5 mm is assumed to occupy inside the subject. Note that the background tissue B2 other than the mammary gland tissue B1 is assumed that mammary glands occupy by 50%. Then a signal value QA obtained by an X-ray transmitted through the mammary gland tissue B1 and a signal value QB obtained by an X-ray transmitted through only the background tissue B2 are calculated, and log (QB)- log (QA) is calculated, as the contrast value. The contrast values defined in Contrast Table T2 are values normalized such that, when a subject with a breast thickness of 40 mm and a mammary gland/fat ratio of 50% is imaged under the application conditions that the target is Mo, the filter is Mo, and the tube voltage is 28 kV, the contrast takes a value of one.

Figure 8:
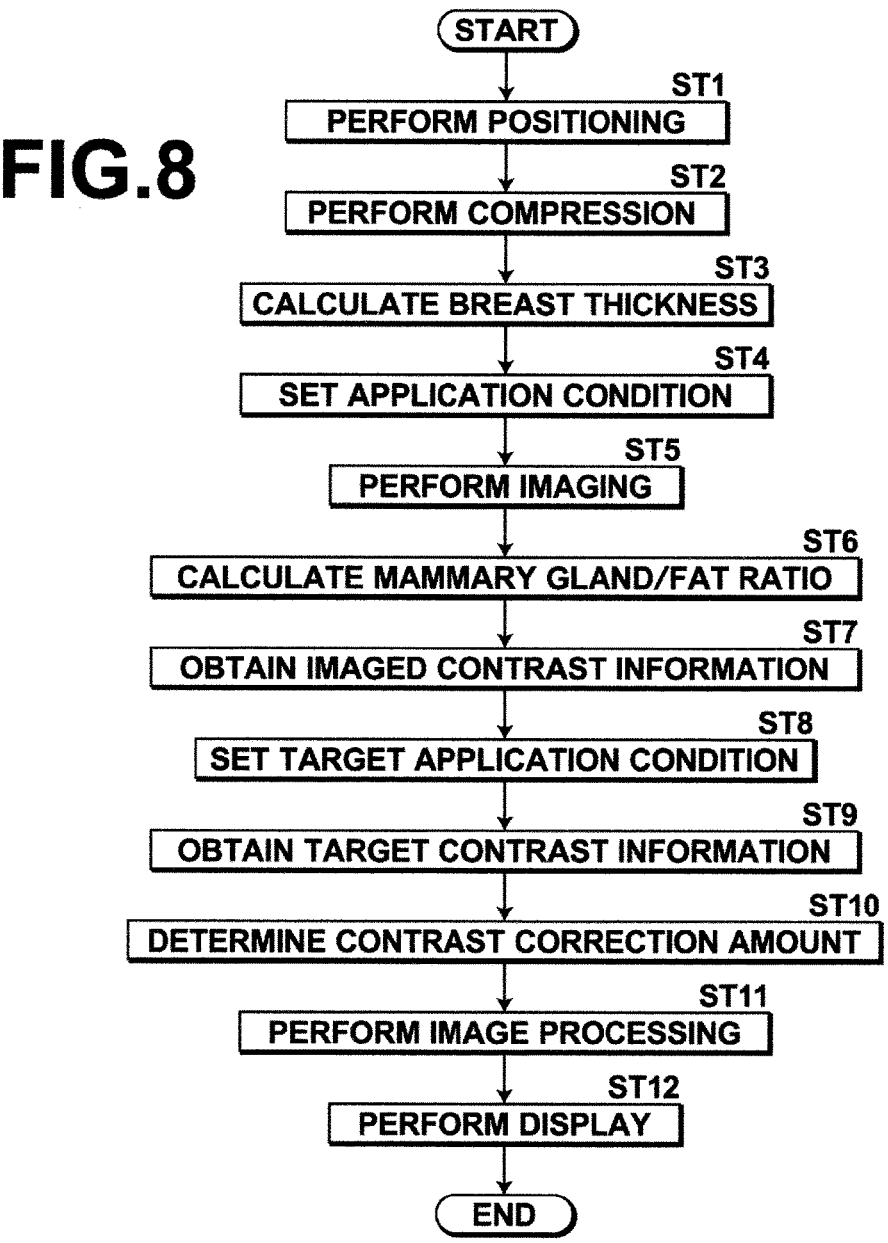
FIG. 8 is a flowchart illustrating the processing performed in the first embodiment.

Next processing performed in the first embodiment will be described. FIG. 8 is a flowchart illustrating the processing performed in the first embodiment. The radiographer performs positioning of a breast M with respect to the imaging platform 40 of the mammography imaging system 14 (step ST1) and compresses the breast M by moving the compression paddle 42 through the compression paddle drive control unit 72 (step ST2). The movement of the compression paddle 42 is stopped when the breast M is compressed to a desired state and the thickness of the breast M at that time is calculated by the thickness calculation unit 78 (step ST3). The thickness calculation unit 78 obtains position information of the compression paddle 42 with respect to the imaging platform 40 from the compression paddle drive control unit 72 and calculates the thickness of the breast M from the position information. The information of the calculate thickness is displayed on the indicator 46, as well as being supplied to the application condition setting unit 80, the first information obtaining unit 84, and the second information obtaining unit 86.

Next, the radiographer sets types of the target 54 and the filter 55, and a tube voltage as application conditions based on the calculated thickness of the breast M. For example, a lower energy X-ray x (softer radiation quality) may result in a higher contrast in the obtained radiation image and the difference between a normal tissue and a diseased tissue of the breast M can be confirmed easily. A higher energy X-ray x (harder radiation quality) may reduce the exposure dose of the breast M and increase the SN of the radiation image as the radiation transmission factor of the breast M is increased. Typically, in the mammography imaging system 14, a priority is given to a high contrast image quality when imaging a thin breast M while a priority is given to the exposure dose that does not exceed a specified value when imaging a thick breast M. But, it is preferable that the exposure dose of the breast M is small. For this reason, the radiographer uses W as the target and Rh as the filter, and sets application conditions such that the tube voltage is appropriate for these materials through manual operations to apply a high energy X-ray x. Further, the radiographer sets a radiation exposure dose (mAs value) required for obtaining an appropriate radiation image, and sets a tube current and a radiation application time that can provide the dose in the source drive control unit 70 as application conditions (application condition setting, step ST4).

When the types of the target 54 and the filter 55, and the tube voltage are set, the application setting unit 80 supplies these application conditions to the source drive control unit 70 of the control apparatus 16. The source drive control unit 70 moves the filament 52 in an arrow A direction in FIG. 3 according to the supplied application conditions to select the target 54. Further, the source drive control unit 70 moves the filter 55 in an arrow C direction in FIG. 3 by driving the filter moving section 66 according to the supplied application conditions to select the filter 55.

When an imaging switch (not shown) is set to ON by the radiographer, the source drive control unit 70 drives the X-ray source 50 and imaging of a radiation image according to the given application conditions is performed (step ST5). The radiation image of the breast M recorded in the solid-state detector 74 by this imaging is read out by the detector control unit 76 and supplied to the image processing apparatus 12.

The composition information obtaining unit 82 of the image processing apparatus 12 calculates a mammary gland/fat ratio based on the radiation image (step ST6). As for the calculation of the mammary gland/fat ratio, for example, the method described in Japanese Unexamined Patent Publication No. 2010-253245 may be used. This method generates a fat image (image having pixel values when all mammary gland tissues are replaced with fat tissues) from the radiation image of the breast M and calculates a mammary gland/fat ratio based on the relationship between the original radiation image and the fat image. The calculation of the mammary gland/fat ratio is not limited to this method and any known method may be used. The information of the mammary gland/fat ratio calculated by the composition information obtaining unit 82 is supplied to the first information obtaining unit 84 and the second information obtaining unit 86 as composition information.

The first information obtaining unit 84 of the image processing apparatus 12 obtains, with reference to Contrast Table T2, imaged contrast information representing a contrast of the radiation image based on the mammary gland/fat ratio, the thickness of the breast M, and the application conditions (step ST7). For example, if the breast thickness is 20 mm, the mammary gland/fat ratio is 50%, the target is W, the filter is Rh, and the tube voltage is 29 kV, reference to Contrast Table T2 in FIG. 6 shows that the imaged contrast information is 0.87.

Figures 9, 10:
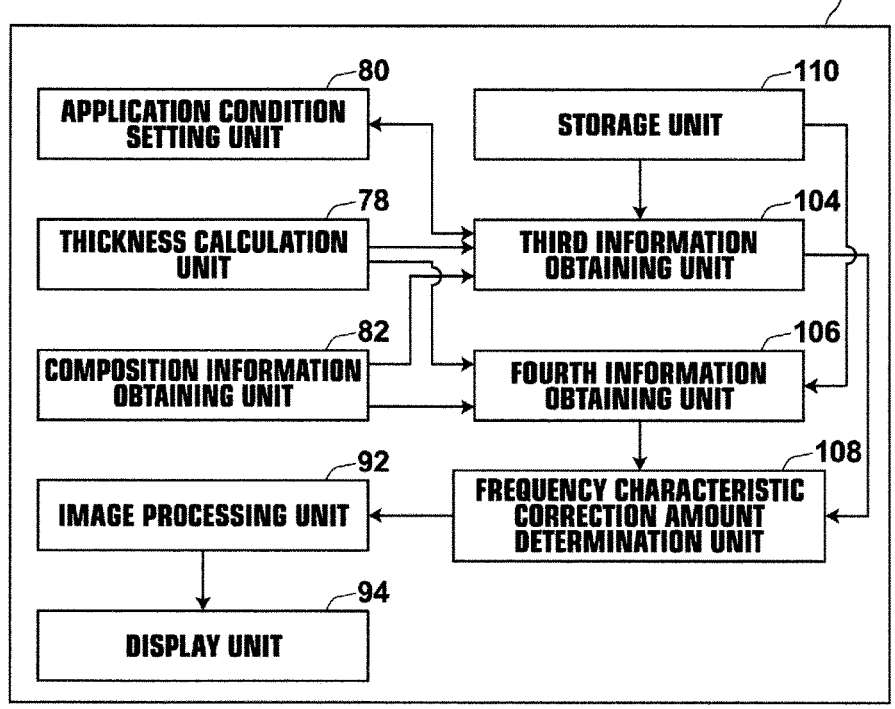
FIG. 9 shows a contrast table.
FIG. 10 is a block diagram of control circuits of an image processing apparatus in a second embodiment.

The second information obtaining unit 86 sets, with reference to Table T1, intended application conditions (target application conditions) for X-ray based on the thickness of the breast M (step ST8), and obtains, with reference to Contrast Table T2, target contrast information representing a contrast of the radiation image based on the mammary gland/fat ratio, the thickness of the breast M, and the application conditions (step ST9). For example, if the thickness of the breast M is 20 mm, the target application conditions are Mo for the target, Mo for the filter, and 26 kV for the tube voltage. Therefore, the second information obtaining unit 86 refers to Contrast Table T2 of Mo/Mo for the target and the filter stored in the storage unit 90 and obtains the target contrast information. A part of Contrast Table T2 of Mo/Mo for the target and the filter with a mammary gland/fat ratio of 50% is shown in FIG. 9. Reference to FIG. 9 shows that the target contrast information is 1.175 by interpolation operation when the thickness of the breast M is 20 mm and the tube voltage is 26 kV.

The contrast amount correction determination unit 88 determines a contrast correction amount based on the imaged contrast information and the target contrast information (step ST10). Here, if the imaged contrast information is 0.87 and the target contrast information is 1.175, the contrast correction amount is determined to be 1.175/0.87≈1.35.

Then, the image processing unit 92 performs image processing, including gradation processing based on the determined contrast correction amount, on the radiation image and obtains a processed radiation image (step ST11). Here, the image processing unit 92 corrects the gradation processing condition based on the determined contrast correction amount. For example, if the contrast correction amount is 1.35, the inclination of the gradation curve, which serves as the gradation processing condition, is increased by 1.35 times. Then, the image processing unit 92 performs gradation processing on the radiation image according to the corrected gradation processing condition. Further, the image processing unit 92 analyzes the gradation-processed radiation image and sets a standardization processing condition, an edge enhancement processing condition, a frequency processing condition, a noise filtering processing condition, a dynamic range adjustment processing condition, and a gradation processing condition for the radiation image. Then, according to the set image processing conditions, the image processing unit 92 performs image processing on the radiation image subjected to the gradation processing according to the corrected gradation processing condition.

The radiation image subjected to the image processing in the manner described above is displayed on the display unit 94 to be confirmed by the radiographer (step ST12), and the processing is completed. The radiation image is stored in the image database 18 and used by a doctor for diagnosis at the terminal unit 20.

In this way, in the first embodiment, imaged contrast information representing a contrast of a radiation image is obtained based on the mammary gland/fat ratio, the thickness of the breast M, and the application conditions, application conditions intended for radiation are set, target contrast information is obtained based on the mammary gland/fat ratio, the thickness of the breast M, and the intended application conditions, and a contrast correction amount for the radiation image is determined based on the imaged contrast information and the target contrast information. Therefore, a radiation image having a desired contrast may be obtained based not only on the application conditions of radiation applied to the subject but also on the mammary gland/fat ratio and the thickness of the breast M by correcting the contrast of the radiation image based on the determined correction amount.

Further, when the imaging system 14 is replaced, the application conditions may differ depending on the imaging system 14 and image qualities of radiation images obtained before and after the replacement may differ. Still further, there may be a case in which desired application conditions cannot be set due to imaging constraints. For example, in the case of chest imaging, the contrast of a bone portion overlapping with a soft portion is preferably reduced by setting the tube voltage to a relatively high value of about 100 kV to 120 kV. Portable imaging performed, for example, in a patient room, however, the tube voltage may be set only to about 80 kV due to imaging constraints. In such a case also, a radiation image having a desired image quality may not be obtained.

In the first embodiment, as the contrast correction amount is determined based on the imaged contrast information and the target contrast information, a radiation image having a desired contrast may be obtained even when the imaging system is replaced. Further, even if there is an imaging constraint, a radiation image having a desired contrast identical to that obtained when imaging is performed under desired application conditions.

Next, a second embodiment of the present invention will be described. Note that the medical image support system which includes a radiation image processing apparatus according to a second embodiment differs from the first embodiment only in the configuration of the image processing apparatus. Therefore, the detailed description for the configuration of the medical image support system is omitted.

FIG. 10 is a block diagram of control circuits of an image processing apparatus in a second embodiment. Note that in the second embodiment, components identical to those of the first embodiment are given the same reference numerals and will not be elaborated upon further here. In an image processing apparatus 12A, the second embodiment includes, in place of the first information obtaining unit 84 and the second information obtaining unit 86, a third information obtaining unit 104 that obtains imaged frequency characteristic information representing a frequency characteristic of the radiation image based on the composition information, the thickness information of the breast M, and the application conditions, a fourth information obtaining unit 106 that sets target application conditions for the X-ray based on the thickness of the breast M and obtains target frequency characteristic information representing an intended frequency characteristic for the radiation image based on the composition information, the thickness of the breast M, and the target application conditions, a frequency characteristic correction amount determination unit 108 that determines a frequency characteristic correction amount based on the imaged frequency characteristic information and the target frequency characteristic information, and storage unit 110 that stores information of target application conditions corresponding to a plurality of thicknesses of the breast M and frequency characteristic information corresponding to a plurality of thicknesses of the breast M, a plurality of application conditions, and a plurality of mammary gland/fat ratios with respect to each combination of target and filter, in which imaging processing, including frequency processing based on the corrected frequency characteristic information, is performed in the image processing unit 92.

In the second embodiment, the storage unit 110 stores Frequency Characteristic Table T3 that defines frequency characteristic information. Frequency Characteristic Table T3 is a three-dimensional table that defines frequency characteristics corresponding to a plurality of breast thicknesses, a plurality of tube voltages, and a plurality of mammary gland/fat ratios with respect to each combination of target and filter. The frequency characteristic as used in the present embodiment represents a response value at a frequency of 2 cycles/mm which is a special frequency of a diagnostic target mammary gland or a lesion such as, for example, calcification. The frequency characteristics defined in Frequency Characteristic Table T3 may be calculated by simulation, as in the contrast. Further, Frequency Characteristic Table T3 may be provided by preparing phantoms corresponding to a plurality of breast thickness and a plurality of mammary gland/fat ratios, imaging the phantoms with a plurality of tube voltages with respect to each combination of target and filter, calculating MTFs (Modulation Transfer Functions) of the radiation images obtained by imaging the phantoms, and defining the response values at the frequency of 2 cycles/mm in the MTFs.

Figure 11:
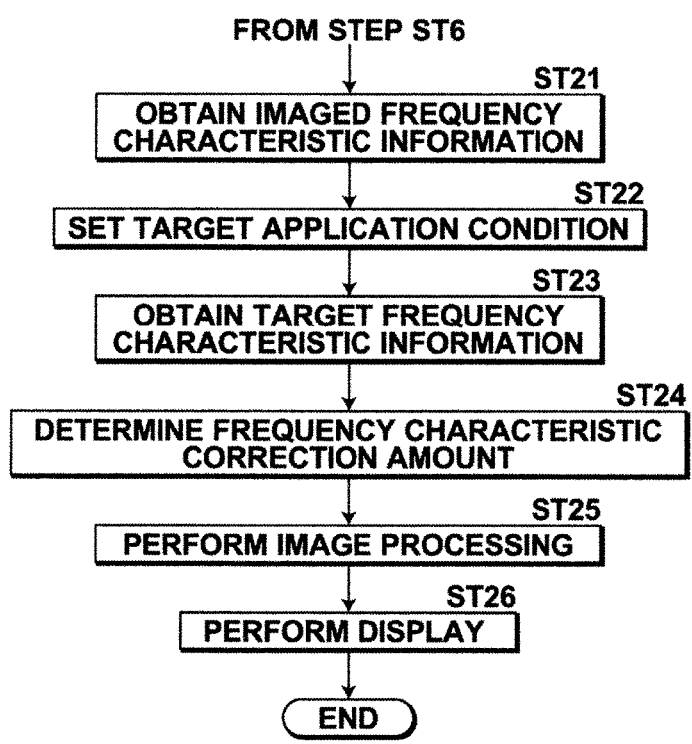
FIG. 11 is a flowchart illustrating the processing performed in the second embodiment.

Next, processing performed in the second embodiment will be described. FIG. 11 is a flowchart illustrating the processing performed in the second embodiment. Note that, in the second embodiment, only the processing steps from the step ST7 onward in the flowchart of the first embodiment are different and, therefore, only the processing steps from step ST7 onward will be described here.

After the mammary gland/fat ratio is calculated by the composition information obtaining unit 82, the third information obtaining unit 104 of the image processing apparatus 12A obtains, with reference to Frequency Characteristic Table T3, imaged frequency characteristic information representing a frequency characteristic of the radiation image based on the mammary gland/fat ratio, the thickness of the breast M, and the application conditions (step ST21).

The fourth information obtaining unit 106 sets, with reference to Table T1, target application conditions based on the thickness of the breast M (step ST22), and obtains, with reference to Frequency Characteristic Table T3, target frequency characteristic information representing an intended frequency characteristic for the radiation image based on the mammary gland/fat ratio, the thickness of the breast M, and the application conditions (step ST23).

The frequency characteristic correction amount determination unit 108 determines a frequency correction amount based on the imaged frequency characteristic information and the target frequency characteristic information (step ST24). For example, if the imaged frequency characteristic information is 0.5 and the target frequency characteristic information is 0.75, the frequency characteristic correction amount is determined to be 1.5.

Then, the image processing unit 92 performs image processing, including frequency processing based on the determined frequency characteristic correction amount, on the radiation image and obtains a processed radiation image (step ST25). Here, the image processing unit 92 performs frequency processing based on the determined frequency characteristic correction amount first. For example, if the frequency characteristic correction amount is 1.5, the image processing unit 92 performs frequency processing such as, for example, filtering processing on the radiation image such that the response at 2 cycles/mm in the radiation image is increased by 1.5 times. Then, the image processing unit 92 analyzes the frequency-processed radiation image and sets a standardization processing condition, an edge enhancement processing condition, a frequency processing condition, a noise filtering processing condition, a dynamic range adjustment processing condition, and a gradation processing condition for the radiation image. Then, according to the set image processing conditions, the image processing unit 92 performs image processing on the radiation image subjected to the frequency processing based on the determined frequency characteristic correction amount.

The radiation image subjected to the image processing in the manner described above is displayed on the display unit 94 to be confirmed by the radiographer (step ST26), and the processing is completed. The radiation image is stored in the image database 18 and used by a doctor for diagnosis at the terminal unit 20.

In this way, in the second embodiment, imaged frequency characteristic information representing a frequency characteristic of a radiation image is obtained based on the mammary gland/fat ratio, the thickness of the breast M, and the application conditions, application conditions intended for radiation are set, target frequency characteristic information is obtained based on the mammary gland/fat ratio, the thickness of the breast M, and the intended application conditions, and a frequency characteristic correction amount is determined based on the imaged frequency characteristic information and the target frequency characteristic information. Therefore, a radiation image having a desired frequency characteristic may be obtained based not only on the application conditions of radiation applied to the subject but also on the mammary gland/fat ratio and the thickness of the breast M by correcting the frequency characteristic of the radiation image based on the determined correction amount.

Next, a third embodiment of the present invention will be described. Note that the medical image support system which includes a radiation image processing apparatus according to a third embodiment differs from the first embodiment only in the configuration of the image processing apparatus. Therefore, the detailed description for the configuration of the medical image support system is omitted.

Figure 12:
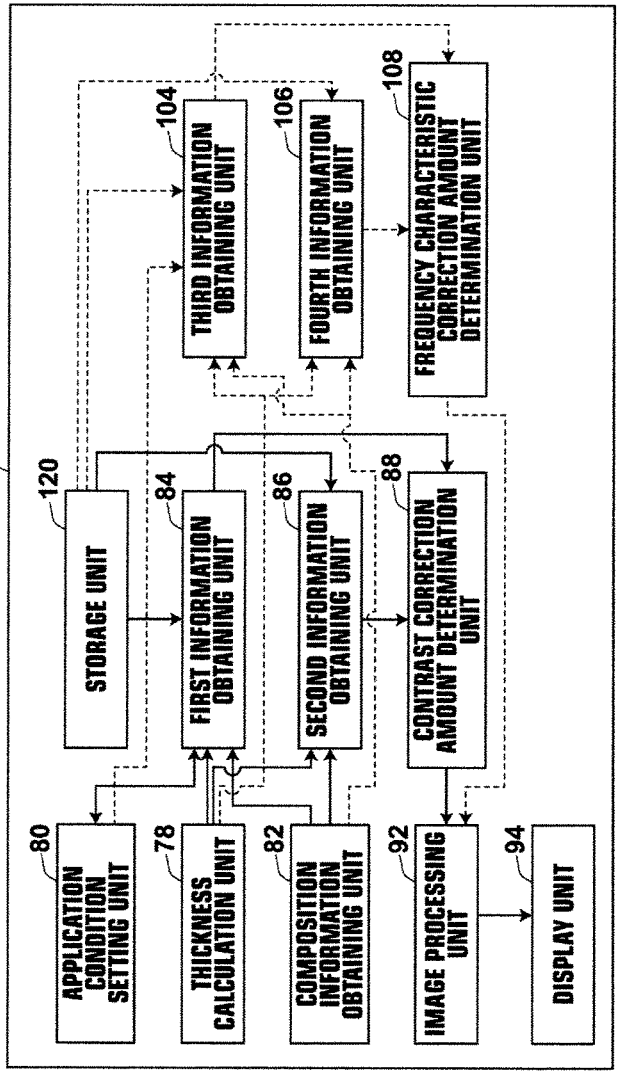
FIG. 12 is a block diagram of control circuits of an image processing apparatus in a third embodiment.

FIG. 12 is a block diagram of control circuits of an image processing apparatus in a third embodiment. Note that in the second embodiment, components identical to those of the first and second embodiments are given the same reference numerals and will not be elaborated upon further here. The third embodiment differs from the first embodiment in that it includes, in an image processing apparatus 12B, the third information obtaining unit 104, the fourth information obtaining unit 106, and the frequency characteristic correction amount determination unit 108, in addition to the first information obtaining unit 84, the second information obtaining unit 86, and the like, in which Table T1, Contrast Table T2, and Frequency Characteristic Table T3 are stored in a storage unit 120 and image processing, including gradation processing based on a corrected contrast and frequency processing based on a corrected frequency characteristic, is performed in the image processing unit 92.

Figure 13:
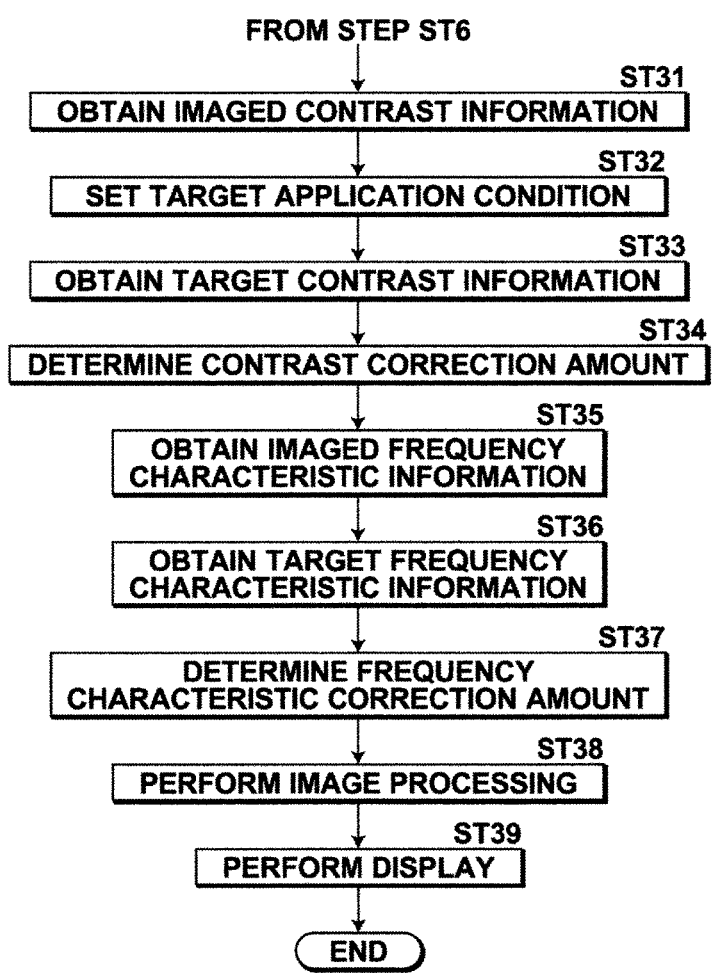
FIG. 13 is a flowchart illustrating the processing performed in the third embodiment.

Processing performed in the third embodiment will be described. FIG. 13 is a flowchart illustrating the processing performed in the third embodiment. Note that, in the third embodiment, only the processing steps from the step ST7 onward in the flowchart of the first embodiment are different and, therefore, only the processing steps from step ST7 onward will be described here.

After the mammary gland/fat ratio is calculated by the composition information obtaining unit 82, the first information obtaining unit 84 of the image processing apparatus 12B obtains, with reference to contrast Table T2, imaged contrast information representing a contrast of the radiation image based on the mammary gland/fat ratio, the thickness of the breast M, and the application conditions (step ST31).

The second information obtaining unit 86 sets, with reference to Table T1, target application conditions for X-ray based on the thickness of the breast M (step ST32), and obtains, with reference to Contrast Table T2, target contrast information representing an intended contrast for the radiation image based on the mammary gland/fat ratio, the thickness of the breast M, and the application conditions (step ST33). Then, the contrast amount correction determination unit 88 determines a contrast correction amount based on the imaged contrast information and the target contrast information (step ST34).

In the meantime, the third information obtaining unit 104 in the image processing apparatus 12B obtains, with reference to Frequency Characteristic Table T3, imaged frequency characteristic information representing a frequency characteristic of the radiation image based on the mammary gland/fat ratio, the thickness of the breast M, and the application conditions (step ST35).

The fourth information obtaining unit 106 obtains, with reference to Frequency Characteristic Table T3, target frequency characteristic information representing an intended frequency characteristic for the radiation image based on the mammary gland/fat ratio, the thickness of the breast M, and the target application conditions obtained by the second information obtaining unit 86 (step ST36). Then, the frequency characteristic correction amount determination unit 108 determines a frequency correction amount based on the imaged frequency characteristic information and the target frequency characteristic information (step ST37).

Either of the processing from the step ST31 to the step ST34 and the processing from the step ST35 to the step ST37 may be performed first or performed in parallel.

Then, with respect to the radiation image, the image processing unit 92 performs gradation processing based on the determined contrast correction amount, as in the first embodiment, and performs image processing, including frequency processing based on the determined frequency characteristic correction amount, as in the second embodiment, and obtains a processed radiation image (step ST38). The radiation image subjected to the image processing in the manner described above is displayed on the display unit 94 to be confirmed by the radiographer (step ST39), and the processing is completed. The radiation image is stored in the image database 18 and used by a doctor for diagnosis at the terminal unit 20.

In this way, in the third embodiment, both the contrast correction amount and the frequency characteristic correction amount are determined based on the mammary gland/fat ratio, the thickness of the breast M, and the application conditions. Therefore, a radiation image having a desired contrast and a desired frequency characteristic may be obtained based not only on the application conditions of radiation applied to the subject but also on the mammary gland/fat ratio and the thickness of the breast M by correcting the contrast and the frequency characteristic of the radiation image based on the determined correction amounts.

As a preferable image quality of a radiation image may differ depending on the doctor that performs radiation image interpretation, the combination of target and filter may sometimes be specified by a doctor at the time of imaging. In the first embodiment described above, target application conditions are set based on the thickness of the breast M using the target application condition setting table T1, but in such a case, target application conditions desired by the radiographer may be set directly without referencing Table T1. In this case, the application conditions at the time of imaging may be determined in advance, and when a desired combination of target and filter and a tube voltage (i.e., target application conditions) are set directly by the radiographer, the second information obtaining unit 86, with reference to Contrast Table T2, obtains target contrast information representing an intended contrast for the radiation image based on the mammary gland/fat ratio, the thickness of the breast M, and the application conditions. This allows, in particular when no combination of target and filter corresponding to a target application condition is present in the imaging system, a radiation image having a contrast identical to that obtained based on the target application condition to be obtained. In this case, an arrangement may be adopted in which a mode representing an image quality and an application condition is associated in advance and application condition is set by the radiographer by setting a desire mode in the imaging system. Further, in this case, an arrangement may be adopted in which the dose is set by a noise condition desired by the radiographer. It should be appreciated that target application conditions may be set directly also in the second and the third embodiments in the same manner.

In the embodiments described above, the imaged contrast information is obtained using even the mammary gland/fat ratio information but an arrangement may be adopted in which the imaged contrast information and target contrast information are obtained using only the thickness of the breast M and the application conditions. In this case, Contrast Table T2 is a two-dimensional table in which contrasts corresponding to a plurality of breast thicknesses and a plurality of tube voltages are defined with respect to each combination target and filter. Likewise, the imaged frequency characteristic information and the target frequency characteristic information may be obtained using only the thickness of the breast M and the application conditions, and in this case, Frequency Characteristic Table T3 is a two-dimensional table in which frequency characteristics corresponding to a plurality of breast thicknesses and a plurality of tube voltages are defined with respect to each combination of target and filter.

Figure 14:
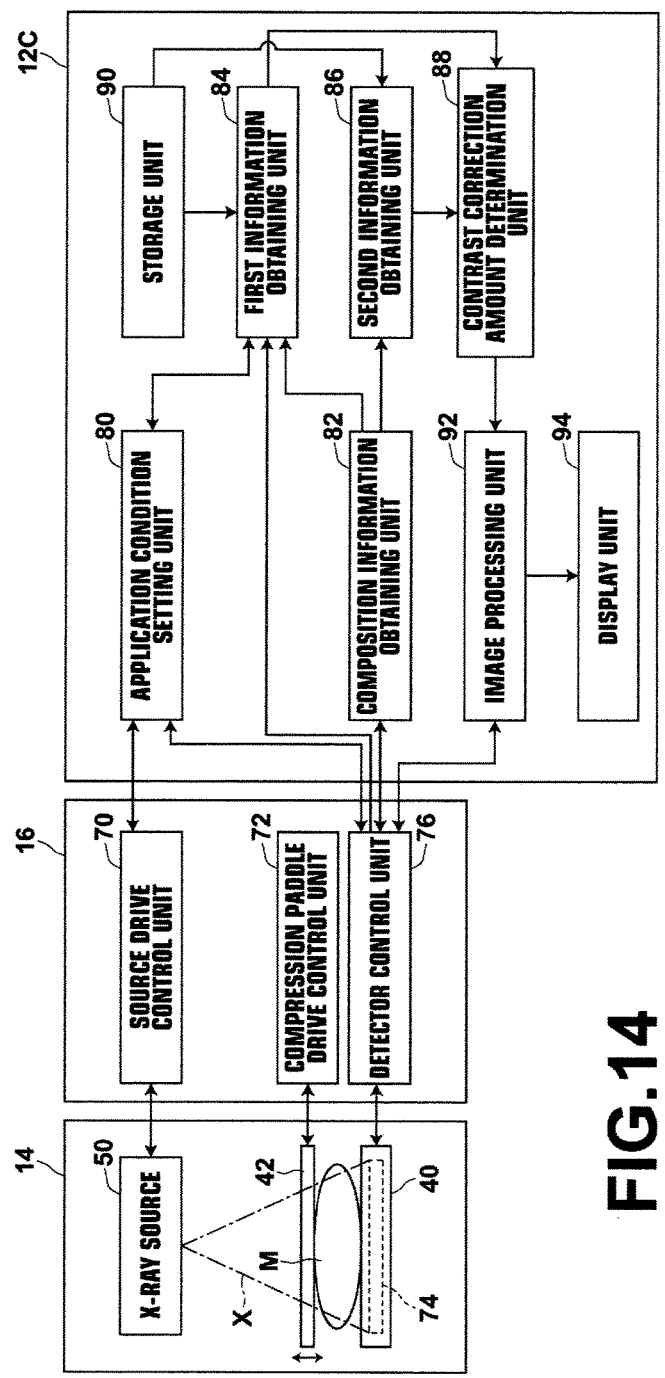
FIG. 14 is a block diagram of control circuits of an image processing apparatus, a mammography imaging system, and a control apparatus according to a fourth embodiment.

In the first embodiment described above, the imaged contrast information is obtained based on the thickness of the breast M and application conditions, but not limited to this, and an arrangement may be adopted in which the imaged contrast information is obtained based on a radiation image obtained by imaging. This will be described hereinafter as a fourth embodiment. FIG. 14 is a block diagram of control circuits of an image processing apparatus, a mammography imaging system, and a control apparatus according to a fourth embodiment. In the fourth embodiment, components identical to those of the first embodiment are given the same reference numerals and will not be elaborated upon further here. The fourth embodiment differs from the first embodiment in that the first information obtaining unit 84 in the image processing apparatus 12C obtains imaged contrast information using a radiation image supplied from the detector control unit 76 and the second information obtaining unit 86 obtains target application conditions and target contrast information without using the thickness of the breast M.

In the fourth embodiment, the first information obtaining unit 84 analyzes a radiation image supplied from the detector control unit 76 and obtains imaged contrast information using, for example, the method described in Japanese Unexamined Patent Publication No. 2010-253245 or Japanese Unexamined Patent Publication No. 2009-247521. More specifically, an area of the breast M which includes many mammary glands is extracted from the radiation image and a local contrast within the extracted mammary gland area is calculated. The first information obtaining unit 84 obtains such a local contrast as the imaged contrast information.

The second information obtaining unit 86 obtains target application conditions. In the fourth embodiment, a radiographer inputs a desired radiation quality (i.e., combination of target and filter) and a tube voltage in the image processing apparatus 12C, as desired target application conditions, and the second information obtaining unit 86 obtains the target application conditions inputted by the radiographer. Then, the second information obtaining unit 86 obtains target contrast information based on the composition information and the target application conditions. More specifically, the second information obtaining unit 86 refers to a table in which target contrasts corresponding to a plurality of tube voltages and a plurality of mammary gland/fat ratios are defined with respect to each combination of target and filter, and calculates the target contrast information based on the inputted target application conditions and the mammary gland/fat ratio calculated in the image analysis.

Then, as in the first embodiment described above, the contrast correction amount determination unit 88 determines a contrast correction amount based on the imaged contrast information and the target contrast information, and the image processing unit 92 performs image processing, including gradation processing based on the contrast correction amount, whereby a processed radiation image is obtained.

In the fourth embodiment described above, an arrangement may be adopted in which the first information obtaining unit 84 obtains imaged contrast information by analyzing a radiation image, and the second information obtaining unit 86 target application conditions and target contrast information using the thickness of the breast M, as in the first embodiment. Contrary to this, an arrangement may be adopted in which the first information obtaining unit 84 obtains imaged contrast information using the thickness of the breast M, as in the first embodiment, and the second information obtaining unit 86 obtains target contrast information based on analysis results of the radiation image, application conditions at the time of imaging, composition information, and target application conditions.

Also, in the third embodiment, an arrangement may be adopted in which the first information 84 obtains imaged contrast information using a radiation image supplied from the detector control unit 76 and the second information obtaining unit 86 obtains target application conditions and target contrast information without using the thickness of the breast M.

Further, in the second and third embodiments, an arrangement may be adopted in which the third information obtaining unit 104 obtains imaged contrast information using a radiation image supplied from the detector control unit 76 and the fourth information obtaining unit 106 obtains target application conditions and target frequency characteristic information without using the thickness of the breast M.

Still further, in the embodiments described above, an arrangement may be adopted in which a pre-radiation image is obtained using low dose radiation prior to obtaining a radiation image, application conditions are set such that the best S/N is obtained for the radiation image by analyzing the pre-radiation image. Then, a radiation image of the subject is obtained under the set application conditions and, as in the embodiments described above, a contrast correction amount is calculated based on the imaged contrast information and the target contrast information, and image processing is performed on the radiation image according to the calculated contrast correction amount. This allows a processed radiation image having a desired contrast to be obtained while noise in the radiation is reduced.

Generally, the breast M is diagnosed by obtaining radiation images of both the left and the right breasts, and the right and the left breasts M are often compared in diagnosis. Therefore, common target contrast information and/or target frequency characteristic information are preferably set for the radiation images of the left and right breasts M. Sometimes, a plurality of radiation images may be obtained for the same breast M by performing imaging from a plurality of imaging directions. In such a case, the plurality of radiation images is often compared in diagnosis. Therefore, common target contrast information and/or target frequency characteristic information are preferably set for the radiation images obtained by performing imaging from the plurality of directions.

Figure 15:
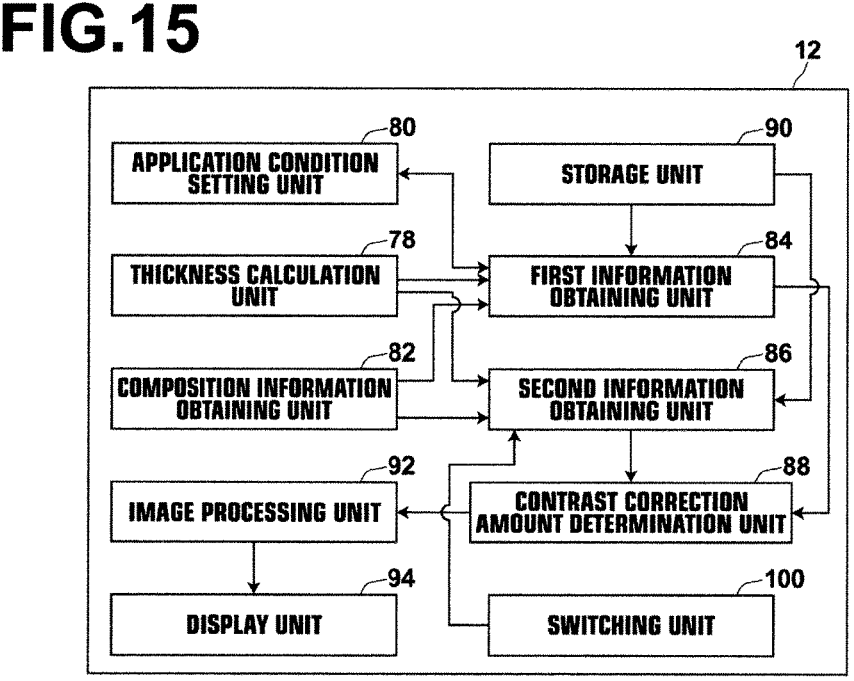
FIG. 15 is a block diagram illustrating an image processing unit equipped with a switching unit.

In the image processing apparatuses 12, 12A, 12B, and 12C according to the embodiments described above, common target contrast information and/or target frequency characteristic information may be set automatically, but the image quality of a plurality of image to be compared can sometimes be different. Thus, a switching unit 100 that switches whether or not to automatically set common target contrast information and/or target frequency characteristic information may be provided in the image processing apparatus 12, as shown in FIG. 15. This allows switching between automatic and non-automatic settings of common target contrast information and/or target frequency characteristic information.

Further, in the embodiments described above, the thickness calculation unit 78 calculates the thickness of the breast M from the position information of the compression paddle 42 with respect to the imaging platform 40, but the calculation of the thickness of the breast M is not limited to this. For example, in the imaging system 14, the distance (SID) between the X-ray source 50 and the detection surface of the solid-state detector 74 is known. Further, the distance (SOD) between the X-ray source 50 and the breast M, i.e., the subject, may be known by equipping the imaging system 14 with a distance meter, for example, an ultrasonic meter. Therefore, SID−SOD may be calculated as the thickness of the breast M. Note that the use of SID and SOD allows thickness calculation for a subject other than the breast M.

Still further, the thickness of the breast M may be obtained by analyzing the radiation image. For example, the difference between the maximum and the minimum pixel values within the area of the breast M may be calculated as the dynamic range of the breast M using the method described in Japanese Unexamined Patent Publication No. 2010-253245. Here, as there is a correlation between the dynamic range and the thickness of the breast M, a table that associates thicknesses with dynamic ranges may be provided in advance and the thickness of the breast M may be obtained from the dynamic range by the use of the table.

Further, as there is also a correlation between a pixel value in the area of the breast M in the radiation image and the thickness of the breast M, a table that associates a thickness with a pixel value may be provided in advance and the thickness of the breast M may be obtained from the pixel value by the use of the table.

Figure 16:
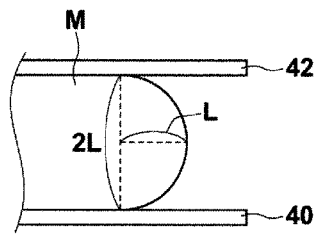
FIG. 16 is a drawing for explaining thickness calculation of a breast.
Figure 17:
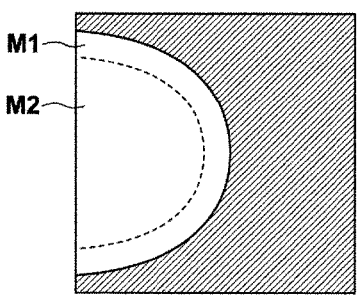
FIG. 17 is a drawing for explaining thickness calculation of a breast.

As the breast M is compressed by the compression paddle 42 when imaging the breast M, a peripheral portion of the breast M has a semicircular shape in cross-section, as illustrated in FIG. 16. In a radiation image of the breast M imaged in such a compressed state, a portion M1 where the breast M has a semicircular shape in cross-section differs in pixel value form a portion M2 contacting the compression paddle 42, as illustrated in FIG. 17. For this reason, the area of the breast M in the radiation image is divided into two portions of M1 and M2 by a clustering method, for example, k-means method. Then, the distance L from the skin line of the breast M at the boundary between the portion M1 and the portion M2 is calculated and the value 2L which is the twice of the distance L is calculated as the thickness of the breast M, as illustrated in FIG. 16.

Figure 18:
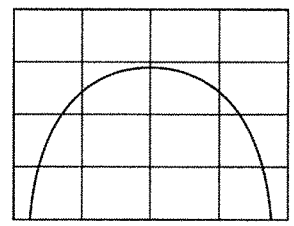
FIG. 18 illustrates a radiation image divided into a plurality of areas.

Further, in the embodiments described above, a contrast correction amount is set over the entirety of a radiation image, but an arrangement may be adopted in which a radiation image is divided into a plurality of areas, as shown in FIG. 18, a mammary gland/fat ratio is calculated for each area, imaged contrast information and target contrast information are obtained for each area with reference to Contrast Table T2 to determine a contrast correction amount. In the example shown in FIG. 18, the contrast correction amount may be determined for only an area of the radiation image where the breast M is present. Further, the area division is not limited to that shown in FIG. 18 and, for example, the radiation image may be divided into a plurality of areas according to the mammary gland/fat ratio. More specifically, the radiation image may be divided into five areas, like an area with a mammary gland/fat ratio of 0 to 20%, an area with a mammary gland/fat ratio of 20 to 40%, an area with a mammary gland/fat ratio of 40 to 60%, an area with a mammary gland/fat ratio of 60 to 80%, and an area with a mammary gland/fat ratio of 80 to 100%, and the contrast correction amount may be determined with respect to each area. Likewise, it should be appreciated that the radiation image may be divided into a plurality of areas and the frequency characteristic correction amount may be determined with respect to each area.

Figure 19:
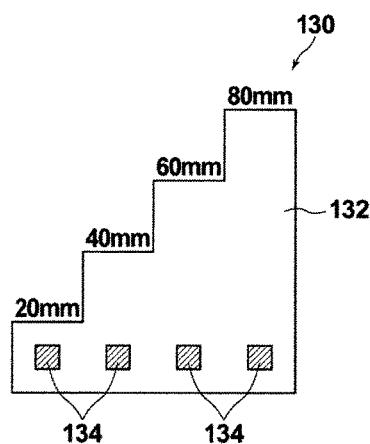
FIG. 19 illustrates a calibration phantom.

In the mammography imaging system 14 used in the embodiments described above, the contrast of a radiation image may sometimes change due to time deterioration of the X-ray source 50, parts replacement, and the like. In this case, appropriate image processing conditions are also changed and, therefore, regular calibration of Contrast Table T2 is preferable. The calibration is performed using a calibration phantom having known X-ray absorption characteristics. FIG. 19 illustrates the structure of the calibration phantom. As illustrated in FIG. 19, the calibration phantom 130 includes a main body 132 formed so as to have different thicknesses of 20 mm, 40 mm, 60 mm, and 80 mm in a stepwise manner in which mammary gland representations 134 having a predetermined thickness (e.g., 5 mm) are embedded at the respective thicknesses. The main body 132 is made of a material, for example, a resin having radiation transmission characteristics comparable to those in the case in which mammary glands occupy by 50% and the mammary gland representation 134 is made of a mammary gland equivalent material, for example, a resin having radiation transmission characteristics comparable to those in the case in which mammary glands occupy by 100%.

In performing calibration, such a phantom 130 is placed on the imaging platform of the mammography imaging system 14, and radiation is applied to the phantom 130 from above in FIG. 19 to image the phantom 130. In this case, imaging is performed by setting application conditions with respect to all combinations of target and filter defined in Contrast Table T2 with combination of each of tube voltages of 23 kV, 28 kV, and 35 kV, and a radiation image of the phantom 130 is obtained with respect to each application condition. Then, with respect to each thickness of the phantom 130, pixel values of a portion where the radiation has passed through the mammary gland representation 134 and a portion where the radiation has not passed through the mammary gland representation 134 are obtained.

Figure 20:
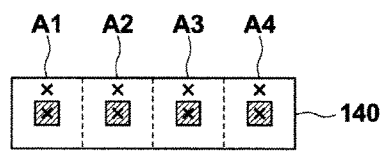
FIG. 20 illustrates an image of the calibration phantom.

FIG. 20 illustrates an image of a calibration phantom. In performing calibration, pixel values QC1 and QC2 are obtained with respect to eight portions in total indicated by the mark×where radiation has and has not passed through the mammary gland representation 134 in four areas of A1 to A4 corresponding to the respective thicknesses of a calibration phantom 140, as illustrated in FIG. 20. Then, in each of the areas A1 to A4, log (QC2)−log (QC1) is obtained as the contrast value. Then, the contrast values are normalized such that, when imaging is performed under the application conditions that the target is Mo, the filter is Mo, and the tube voltage is 28 kV, the contrast takes a value of one. Here, as the tube voltages used in the calibration are discrete as 23 kV, 28 kV, and 35 kV, the contrasts at 25 kV, 27 kV, 29 kV, 31 kV, and 33 kV included in Contrast Table T2 are calculated by interpolation operations, whereby a new Contrast Table T2 is generated and the calibration is completed.

In this way, the regular calibration of Contrast Table T2 may prevent a contrast change due to aging. It should be appreciated that calibration can be performed with respect to Frequency Characteristic Table T3 in a similar way.

Further, when imaging a radiation image, a grid may sometimes be used for preventing radiation incident on the solid-state detector from scattering, the contrast and the frequency characteristics of a radiation image are different between the case in which the grid is used and the case in which the grid is not used. Therefore, Contrast Table T2 and Frequency Characteristic Table T3 are preferably provided according to the presence and absence of the grid.

Still further, in the embodiments described above, the subject is a breast, but not limited to this, and any region of a human body, for example, chest, abdomen, head, or limbs may be the subject. In this case, Contrast Table T2 and Frequency Characteristic Table T3 may be provided by performing a simulation according to the subject. As for the contrast value in Table T2 and Table T3, the contrast between a soft portion and a bone portion may be used, in place of the contrast between the mammary gland/fat ratio of 50% and 100% when the subject is a breast. As for the composition, an area ratio between a bone tissue and a soft tissue may be used in place of the mammary gland/fat ratio.

It should be appreciated that the present invention is not limited to those examples described above, and various changes and modifications may be made without departing from the spirit of the present invention.

What is claimed is:

1. A radiation image processing apparatus, comprising:
a radiation image obtaining unit that obtains a radiation image of a subject;
a first information obtaining unit that obtains imaged contrast information representing a contrast of the radiation image;
a second information obtaining unit that sets an intended application condition of the radiation, and obtains target contrast information representing an intended contrast for the radiation image based on the intended application condition;
a contrast correction amount determination unit that determines a contrast correction amount for the radiation image based on the imaged contrast information and the target contrast information; and
an image processing unit that performs image processing, including gradation processing based on the determined contrast correction amount, on the radiation image and obtains a processed radiation image.

2. The radiation image processing apparatus as claimed in claim 1, wherein the first information obtaining unit is a unit that obtains the imaged contrast information based on a thickness of the subject and an application condition of the radiation at the time of obtaining the radiation image.

3. The radiation image processing apparatus as claimed in claim 1, wherein the second information obtaining unit is a unit that sets the intended application condition based on a thickness of the subject, and obtains the target contrast information based on the thickness of the subject and the intended application condition.

4. The radiation image processing apparatus as claimed in claim 2, further comprising a storage unit that stores intended application condition information corresponding to a plurality of the thicknesses of the subject and contrast information corresponding to the plurality of thicknesses of the subject and a plurality of the application conditions, wherein:
the first information obtaining unit is a unit that obtains the imaged contrast information with reference to the contrast information stored in the storage unit; and
the second information obtaining unit is a unit that sets the intended application condition with reference to the application condition information, and obtains the target contrast information with reference to the contrast information stored in the storage unit.

5. The radiation image processing apparatus as claimed in claim 2, further comprising a composition information obtaining unit that obtains composition information of the subject, wherein:
the first information obtaining unit is a unit that obtains the imaged contrast information based also on the composition information; and
the second information obtaining unit is a unit that obtains the target contrast information based also on the composition information.

6. The radiation image processing apparatus as claimed in claim 5, wherein the composition information is ratio information of a plurality of compositions contained in the subject.

7. The radiation image processing apparatus as claimed in claim 5, further comprising a storage unit that stores intended application condition information corresponding to a plurality of the thicknesses of the subject and contrast information corresponding to the plurality of thicknesses of the subject and a plurality of the application conditions; wherein:
the first information obtaining unit is a unit that obtains the imaged contrast information with reference to the contrast information stored in the storage unit; and
the second information obtaining unit is a unit that sets the intended application condition with reference to the application condition information, and obtains the target contrast information with reference to the contrast information stored in the storage unit.

8. The radiation image processing apparatus as claimed in claim 5, wherein the subject is a breast and the composition is a mammary gland/fat ratio.

9. The radiation image processing apparatus as claimed in claim 1, further comprising:
a third information obtaining unit that obtains imaged frequency characteristic information representing a frequency characteristic of the radiation image;
a fourth information obtaining unit that obtains target frequency characteristic information representing an intended frequency characteristic for the radiation image based on the intended application condition; and
a frequency characteristic correction amount determination unit that determines a frequency characteristic correction amount for the radiation image based on the imaged frequency characteristic information and the target frequency characteristic information.

10. The radiation image processing apparatus as claimed in claim 9, wherein the third information obtaining unit is a unit that obtains the imaged frequency characteristic information based on the thickness of the subject and the application condition.

11. The radiation image processing apparatus as claimed in claim 9, wherein the fourth information obtaining unit is a unit that sets the intended application condition based on the thickness of the subject, and obtains the target frequency characteristic information based on the thickness of the subject and the intended application condition.

12. The radiation image processing apparatus as claimed in claim 1, wherein the subject is a breast, and if a plurality of different radiation images is obtained for the breast, the second information obtaining unit is a unit that obtains target contrast information common to the plurality of radiation images.

13. The radiation image processing apparatus as claimed in claim 12, further comprising a switching unit that switches whether or not to obtain the target contrast information common to the plurality of radiation images.

14. A radiation image processing method, comprising the steps of:
obtaining a radiation image of a subject;
obtaining imaged contrast information representing a contrast of the radiation image;
setting an intended application condition of the radiation, and obtaining target contrast information representing an intended contrast for the radiation image based on the intended application condition;
determining a contrast correction amount for the radiation image based on the imaged contrast information and the target contrast information;
performing image processing, including gradation processing based on the determined contrast correction amount, on the radiation image; and
obtaining a processed radiation image.

* * * * *